United States Patent [19]

Petre et al.

[11] 4,392,849

[45] Jul. 12, 1983

[54] INFUSION PUMP CONTROLLER

[75] Inventors: John H. Petre; Delos M. Cosgrove, both of Cleveland Hts., Ohio

[73] Assignee: The Cleveland Clinic Foundation, Cleveland, Ohio

[21] Appl. No.: 287,516

[22] Filed: Jul. 27, 1981

[51] Int. Cl.³ .............................................. A61M 5/00
[52] U.S. Cl. .......................................... 604/66; 604/50
[58] Field of Search ..................... 128/213 R, 630, 670, 128/905, 272, 260, DIG. 13; 364/415, 416; 604/50, 65, 66, 67, 245

[56] References Cited

U.S. PATENT DOCUMENTS

| 4,080,966 | 3/1978 | McNally et al. | 128/DIG. 13 |
| 4,146,029 | 3/1979 | Ellinwood | 128/260 |
| 4,189,765 | 2/1980 | Kotalik et al. | 364/185 |
| 4,280,494 | 7/1981 | Cosgrove | 128/213 R |

Primary Examiner—Richard J. Apley
Assistant Examiner—George Yanulis
Attorney, Agent, or Firm—Fay & Sharpe

[57] ABSTRACT

A closed loop medication introduction system controls the rate at which medication is introduced into a patient in response to a monitored physiological condition. The system includes a monitor for monitoring the level or magnitude of the physiological condition and an infusion pump for introducing medication for controlling the selected physiological condition into the patient at a variably controllable rate. A controller controls the infusion pump in response to monitored changes in the physiological condition of the patient. A display means displays various information about the monitored physiological condition and the introduction of medication into the patient. The controller produces a rate control signal for controlling the infusion pump in response to signals from the monitor. After an increase in the medication introduction rate, the controller blocks subsequent increases until a sufficient time has passed for the patient to respond to the increase in the amount of medication. If during this time the patient's blood pressure stabilizes, the controller increases the time allowed for the patient to respond to the increased amount of medication. If during this time the patient's blood pressure increases still further, the controller makes a small, interim rate increase. If the patient's blood pressure decreases below the preselected level, the controller decreases the medication introduction rate.

19 Claims, 4 Drawing Figures

INFUSION PUMP CONTROLLER

BACKGROUND OF THE INVENTION

This application pertains to the art of controlling the introduction of medications to patients in response to the patient's physiological conditions or responses. The invention is particularly applicable to apparatus for automatically controlling a patient's blood pressure through automatic adjustments in the infusion rate of a blood pressure controlling medication in response to samplings of the patient's blood pressure and will be described with particular reference thereto. However, it will be appreciated that the invention has other applications such as infusing medications to control other physiological conditions including pulse rate, pulmonary rate, levels of body secreted substances in the blood, and the like.

Commonly, the postoperative care of cardiac surgery patients includes the administration of medications to maintain a consistent and non-hypertensive blood pressure level. This is commonly accomplished by the titration of a vasodilating medication such as Nipride. By controlling the infusion rate of Nipride, the patient's peripheral resistance can be regulated which permits control of the patient's blood pressure levels.

The infusion of Nipride is accomplished with an adjustable infusion pump. The adjustment of the medication infusion rate of the infusing pump is a complicated procedure carried out by the attending nurse. The attending nurse selects an approximate infusion rate and observes the effect on the patient's blood pressure. From the change in the patient's blood pressure level, the nurse determines a change or correction to the infusion rate. This process continues in an attempt to reach a blood pressure level which is close to a preselected, desired blood pressure level.

Many variables make this procedure both difficult and inefficient. Physiological factors influence the blood pressure levels of the patient, in some instances causing the pressure to change rapidly and in others causing the pressure to drift slowly up or down. These factors include age, weight, consciousness, blood volume, history of hypertension, and the like. The maintenance of the preselected blood pressure level is further complicated by the time-delayed response of the patient to Nipride. The effects of a given dose may not be observed for several minutes.

In most instances, the attending nurse also cares for other patients and must make adjustments as often as time permits. The drifting of the patient's blood pressure level between adjustments results in periods in which the patient's blood pressure is higher than the preselected range of blood pressure levels and periods in which it is lower than the desired range of blood pressure levels.

Heretofore, the experience of the attending nurse has been the primary factor in the accuracy with which the patient's blood pressure is controlled. Although the desirability of automatically controlling an infusion pump in response to the patient's blood pressure has been long recognized, the goal of controlling it within an acceptable range of blood pressure levels has been elusive.

The present invention contemplates an apparatus for automatically controlling the rate at which medication is introduced to the patient which overcomes the above-referenced problems and others. Yet, it provides a controller which controls infusion pumps and other medication introducing devices with a high degree of accuracy and reliability.

SUMMARY OF THE INVENTION

In accordance with the present invention, there is provided a method of controlling the rate at which medication is introduced into a patient in response to changes in a physiological condition of that patient. The method includes the following steps: (a) monitoring the physiological condition and producing monitor signals which indicate the level of the physiological condition; (b) comparing the monitor signal with a predetermined level of the physiological condition; (c) if the monitor signal exceeds the predetermined level, determining whether the monitor signals are increasing or decreasing; (d) if the monitor signals are increasing, increasing the medication introduction rate; (e) after each determination in step (c) of whether the monitor signals are increasing or decreasing, incrementing a response interval count; (f) comparing the response interval count with a predetermined interval count; (g) if the response interval count is equal to or greater than the predetermined interval count, increasing the medication introduction rate; (h) if the response interval count is less than the predetermined interval count and after step (g), returning to step (a); (i) if the monitor signal is less than the predetermined level, determining whether the monitor signals are increasing or decreasing; (j) if the monitor signals are decreasing in step (i), decreasing the medication introduction rate; and (k) if the monitor signals are increasing in step (i) and after step (j), returning to step (a).

In accordance with another aspect of the invention, a medication introduction rate control system is provided which includes a blood pressure monitor for monitoring the patient's blood pressure, an analog to digital converter operatively connected with the monitor for producing digital monitor signals which are indicative of the patient's blood pressure, a computer means for deriving from the monitor signals a rate control signal which indicates a rate of medication introduction, a latch means for temporarily storing the rate control signal, and an infusion pump for introducing blood pressure controlling medication into the patient. In accordance with a more limited aspect of the invention, the computer means is programmed to perform the above recited method.

In accordance with yet another aspect of the present invention, there is provided a closed loop medication introduction control system for controlling the rate at which medication is introduced into a patient responsive to changes in the physiological condition of that patient. In the system, a monitor monitors the level of the physiological condition and produces monitor signals which vary with changes in the monitored physiological condition level. Medication introducing means are provided for introducing medication into the patient at a controllable medication introduction rate. A rate controlling means variably controls the medication introduction rate. A comparator means compares the monitor signal with a preselected level of the physiological condition. The comparator means has a first comparator output which is operatively connected with the rate controlling means for increasing the medication introduction rate when the monitor signal exceeds the preselected level and a second comparator output which is operatively connected with the rate controlling means for decreasing the medication introduction rate when the preselected level exceeds the monitor signal. Limiting means which are operatively connected between the first comparator ouput and the rate controlling means limit the time interval between successive medication introduction rate increases to a preselected minimum interval. Rate of change means determine the rate of change of the monitor signals. The rate of change means has a first output for indicating that the monitor signals are increasing and a second output for indicating that the monitor signals are decreasing. The rate of change means is operatively connected with the rate controlling means for adjusting the medication introduction rate in response to the determined rate of change.

A principal advantage of the present invention is that it automatically controls a patient's blood pressure level without the need for monitoring by an attending nurse.

Another advantage of the present invention is that it provides a means for controlling the patient's blood pressure with a relatively high level of accuracy.

BRIEF DESCRIPTION OF THE DRAWINGS

The invention may take form in various parts and arrangements of parts. The drawings illustrate a preferred embodiment of the invention only and are not to be construed as limiting the invention.

DESCRIPTION OF THE PREFERRED EMBODIMENT

Figure 1:
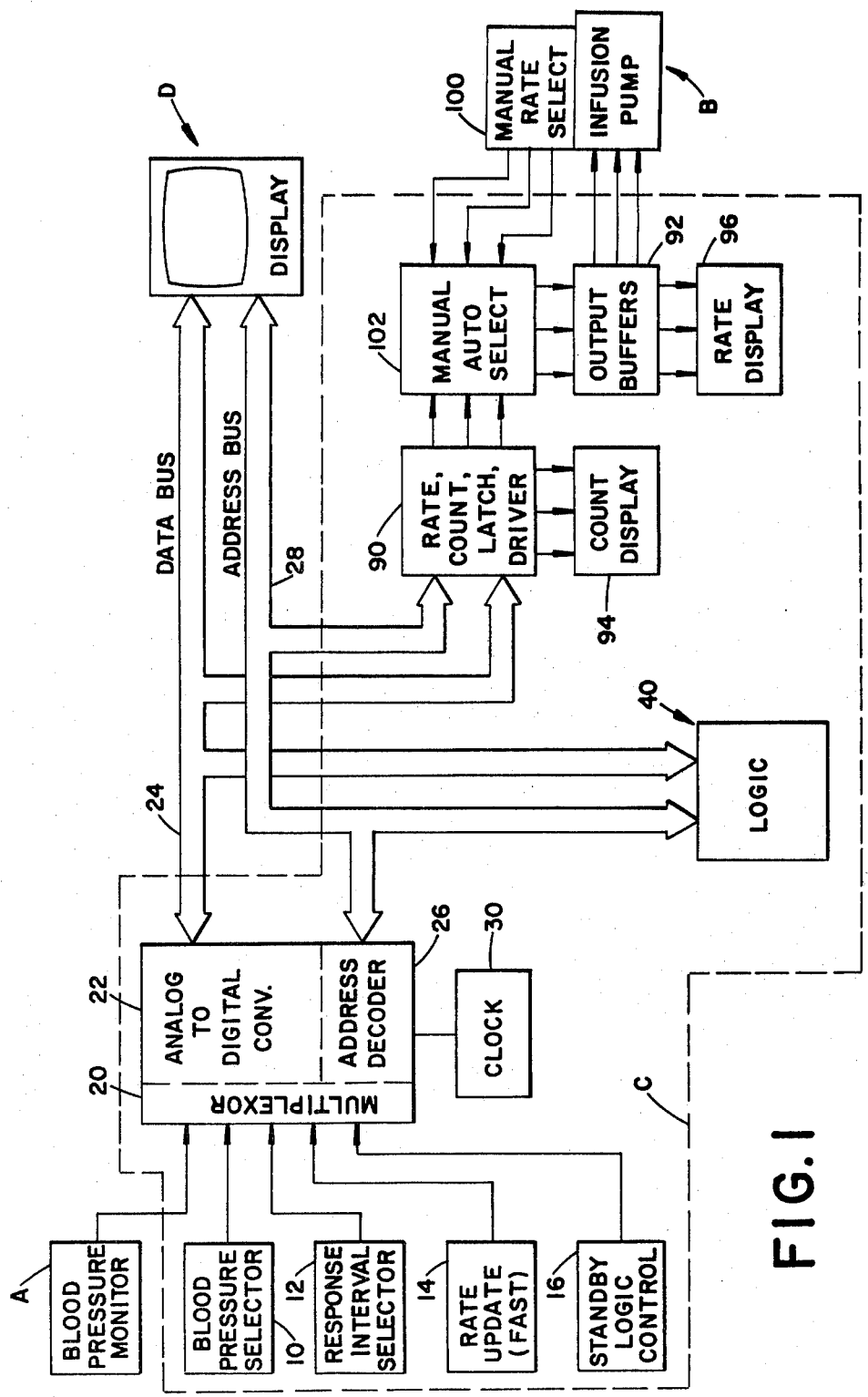
FIG. 1 is a block diagram of a circuit for carrying out the present invention.

FIG. 1 illustrates a closed loop, medication introduction control system for controlling the rate at which medication is introduced into a patient. The system includes a physiological condition monitor A for monitoring the level or magnitude of a physiological condition or response of the patient. In the preferred embodiment, the monitor produces an analog monitor signal which varies with changes in the level of the monitored physiological condition, specifically the patient's blood pressure. Suitable blood pressure monitors include models IM, OM, M2100 Series blood pressure monitors from Electronics for Medicine, Inc. of Pleasantville, N.Y., a subsidiary of Honeywell Corporation and Model SM, Series SM7067 of Statham Instrument Division of Gould, Inc., Oxnard, Calif. A medication introducing means B introduces medication for controlling the selected physiological condition into the patient at a variably controllable rate. In the preferred embodiment, the medication introduction means is an infusion pump for intravenously injecting medication into the patient. An infusion pump with a controllable rate of between 0 and 100 drops per minute has been found to be suitable when using Nipride to control blood pressure. The controllable rate which is desirable will, of course, vary with the medication chosen as well as its dilution or concentration. A suitable infusion pump is the Model #922 or Model #928 from IMED Infusion Pump of San Diego, Calif. A controller C controls the medication introducing means B in responses to the monitored changes in the physiological condition level of the patient. A display means D displays various operating parameters as may be desired. In the preferred embodiment, the display means displays the monitored blood pressure level, the rate at which medication is being introduced into the patient, and other system parameters and selectable or desired levels which will become more apparent in the detailed description of the system below. In the preferred embodiment, the display means D is a video monitor which can change its display rapidly to reflect the current value of changing physiological condition levels and the like. Other display means such as CRT's, LED's, meters, gauges, and the like may alternately be utilized.

Briefly stated, the controlling means C derives from the monitor signal a rate control signal which indicates a desired rate of medication introduction. The magnitude of the rate control signal controls the infusion pump B. After an increase in the medication introduction rate, the controller C blocks a subsequent increase until a sufficient time has passed for the patient to respond to the increased amount of medication. Because this response time is commonly on the order of a minute to a minute and one half, the controller further has provisions for making interim adjustments in the medication introduction rate. If the patient's blood pressure decreases, the controller decreases the medication introduction rate. If the patient's blood pressure stabilizes, the controller increases the duration for which increases in the medication introduction rate are blocked. If the patient's blood pressure increases, the controller may make an interim rate increase during the response period.

Looking to the controller C in more detail, the controller includes a blood pressure selector switch 10 on which the physician or attending nurse may select a desired blood pressure level for the patient being monitored. A response time selector switch allows selection of the duration which is to be allowed for the patient to respond to an increase in medication. A rate update switch 14 permits the medication introduction rate to be increased or decreased manually. A standby logic control switch 16 permits adjustments to be made in the controlling logic.

The outputs of the blood pressure monitor A, the blood pressure selector switch 10, the response time selector switch 12, the rate update switch 14, and the standby logic control switch 16 are conveyed to a multiplexer 20 which cyclically connects each of these outputs to an analog to digital converter 22. The analog to digital converter provides a digital indication of the sampled input signal on a data bus 24. An address decoder 26 causes the multiplexer 20 to move cyclically through its inputs and provides an address signal on an address bus 28 which indicates which of the inputs to the multiplexer is being sampled by the analog to digital converter 22 and being transmitted on the data bus 24. A clock 30 causes the address decoder to step periodically through its cyclic rotation. In its steady state operating mode, it is to be appreciated that all multiplexor inputs need not be sampled in every cycle.

Figure 2:
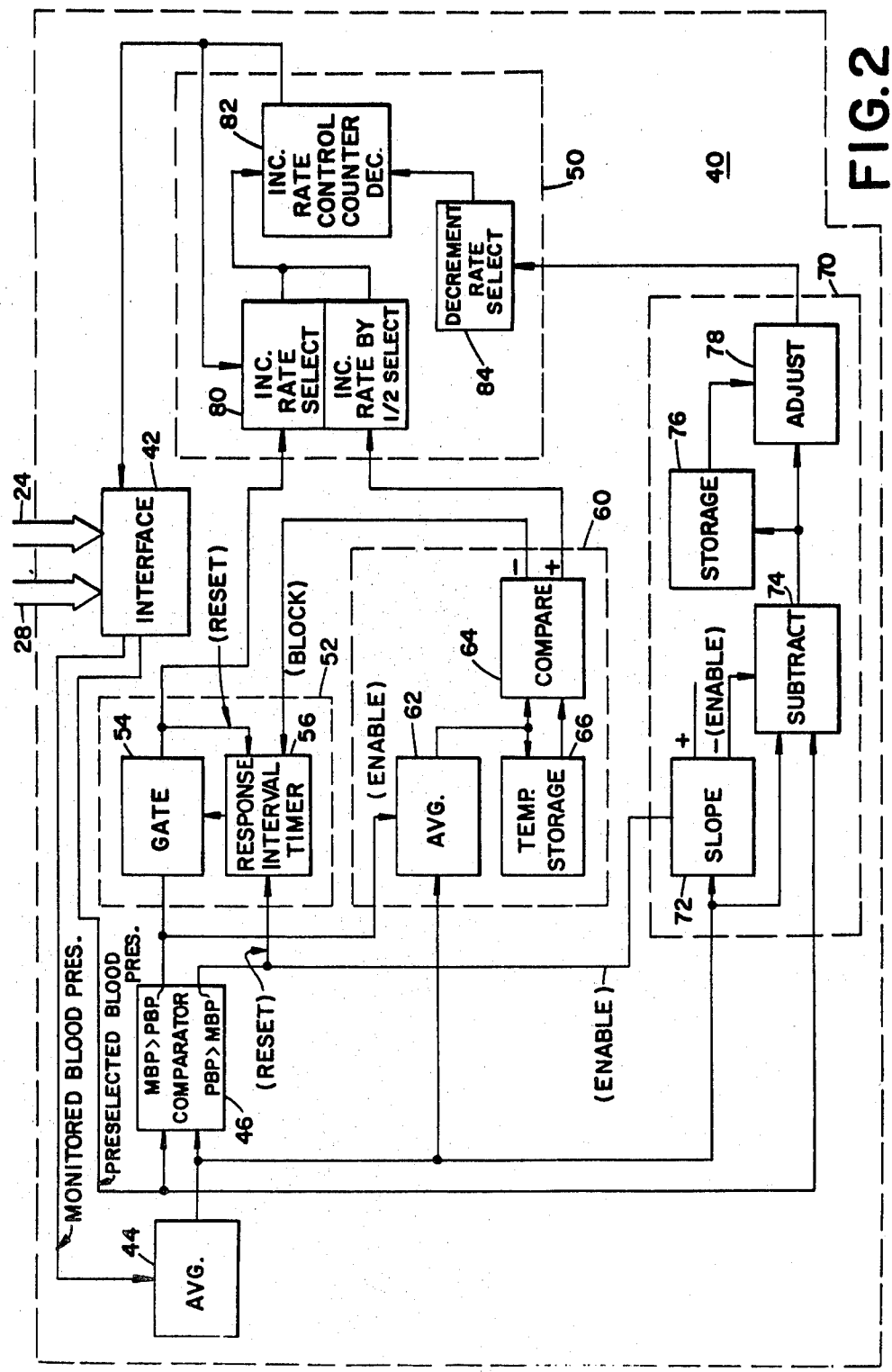
FIG. 2 is a block diagram of a circuit for implementing the logic means of FIG. 1.

The address bus and the data bus are connected with a logic means 40. To facilitate a complete understanding of the invention, the logic means 40 is explained in terms of a hard wired system in conjunction with FIG. 2 and in terms of a programmed microcomputer in conjunction with FIGS. 3A and 3B, below. With reference to FIG. 2, the address bus and data bus are connected with an interface means 42 which uses each received address to direct the data from the data bus to the appropriate portion of the logic means. To improve reliability and accuracy, the monitor signals indicating the patient's blood pressure level are conveyed to an averaging means 44 which averages a plurality, e.g., twenty, monitor blood pressure signals to produce an averaged monitor signal. The blood pressure level selected by the blood pressure selector switch 10 is conveyed to a comparator 46 which compares this preselected level and the monitor signal to determine whether the monitor signal exceeds the preselected level by at least a predetermined minimum or whether the preselected level exceeds the monitor signal by a predetermined minimum. The predetermined minimums provide a deadband range in which the preselected level and monitor signals are sufficiently close that it is deemed undesirable to change the medication introduction rate. The comparator means 46 has a first comparator output for indicating that the monitor signal exceeds the preselected level and a second comparator output for indicating that the preselected level exceeds the monitor signal.

The first comparator output which indicates that the monitor signal exceeds the preselected level is connected to a rate controlling means 50 which produces the rate control signal for controlling the medication introduction rate. A signal on the first comparator output causes the rate control signal and the medication introduction rate to be increased. A limiting means 52 is connected between comparator 46 and the rate controlling means 50 for limiting the duration between successive increases in the medication introduction rate to a preselected minimum time interval which is selected by switch 12 to correspond to the patient's response time. In the preferred embodiment, the response time interval is about eighty seconds. The limiting means 52 includes a gate or blocking means 54 for selectively blocking or passing signals from the comparator 46 to the rate controlling means 50. The blocking means 54 is controlled by a response interval timing means 56. When the blocking means 54 passes a signal to the rate controlling means, the response interval time 56 is reset and thereafter causes the blocking means to block signals from passing to the rate controlling means for the preselected response interval. The response interval timing means 56 is connected with the interface means 42 to enable the response interval selector switch 12 to select different response intervals.

During the response interval as indicated above, the patient's physiological level continues to be monitored. If the monitored blood pressure continues to increase further above the preselected level, it may be necessary to increase the medication introduction rate immediately. For this purpose, a rate change means 60 is provided for determining the rate of change or slope of the monitor signals. The rate of change means 60 includes an averaging means 62 which averages a plurality of the averaged monitor signals from averaging means 44, in the preferred embodiment ten of them. This averaging not only improves the signal but also provides for a delay between successive corrections by the rate of change determining means. In the preferred embodiment, an averaged monitor signal is provided by the averaging and delay means 62 about once every twenty five seconds. The averaged monitor signal is compared by a comparing means 64 with the preceding averaged monitor signal which has been stored in a temporary storage means 66. After the comparison is complete, the stored value in temporary storage means 66 is replaced with the most recent averaged monitor signal. If the comparing means 64 finds that the current averaged monitor signal exceeds the preceding averaged monitor signal from temporary storage means 66, it indicates that the slope or rate of change of the monitor signal is increasing. This positive slope indication is conveyed to the rate controlling means 50 to cause the medication introduction rate to be increased. The rate of increase caused by a rate of change means 60 is a predetermined fraction of increase resulting from a signal from limiting means 52, in the preferred embodiment about a half. If the comparing means 64 indicates that the slope is negative, that is that the monitor signals are approaching the selected level, rate of change means 60 causes the response interval of limiting means 52 to be increased. More specific to the preferred embodiment, the comparing means 64 blocks the response interval timing means 56 from progressing until it compares the next averaged monitor signal from the averaging means 62 with the averaged monitor signal in temporary storage 66, about twenty five seconds. The response interval timing means 56 may be blocked or delayed in various ways such as by setting the timing means back a preselected duration, or by stopping it from moving forward.

When the comparator means 46 determines that the monitor signal is below the preselected level, it enables a medication introduction rate decreasing means 70. The decreasing means 70 includes a second rate of change or slope determining means 72 of similar construction to rate of change means 60 for determining whether the monitor signals are continuing to drop below the selected level, i.e., a negative slope, or whether the monitor signals are rising toward the preselected level, i.e., a positive slope. If the rate of change or slope is positive, no adjustment in the medication introduction rate is made. If the slope is negative or constant, i.e., 0, then the second rate of change means 72 enables a difference or subtraction means 74 for determining the magnitude of the difference between the monitor signal and preselected level. This difference provides an indication of how much the medication introduction rate is to be decreased. Because the slope is determined and the subtraction made at intervals which are shorter than the response interval, it is desirable to make a compensation in the amount of decrease in the medication introduction rate to allow time for the patient to respond. For this purpose, a temporary storage means 76 and a difference signal adjustment means 78 are provided so that subsequent decreases in the medication introduction rate are based on the difference between the preceding and the present monitor signals. In this manner, the amount of decrease in the medication introduction rate corresponds to the difference between the present monitor signal and the lowest monitor signal in the preceding response interval so that multiple compensations are not made for the same drop in the monitor signals before the patient has time to respond.

The rate controlling means 50 includes an incremental rate selection or increasing means 80 which determines the magnitude of the increase in the rate control signal. The incremental rate selection means 80 determines the magnitude of the current rate control signal and upon receiving a signal from limiting means 52 causes an increase or ten to twenty percent. Upon receiving a signal from rate of change means 60, the incremental rate selection means causes an increase of five to ten percent. The rate controlling means includes a rate control up/down counter 82. The incremental rate selection means 80 is connected to its up-count input to cause the counter to count up by a corresponding number of steps. The rate controlling means also includes a decremental rate selection means 84 which is connected to the down-count input of the rate control counter. The decremental rate selection means causes the counter to be decremented by an amount as initiated by the signal from the rate decrease means 70. The magnitude of the count from the rate control counter 82 is the rate control signal which determines the speed at which the infusion pump B is operated. The rate control count is conveyed through the interface means 42 to the data bus 28.

Referring again to FIG. 1, the rate control signal or count conveyed by the data bus 24 to the display means D to be displayed to the attending nurse and to a rate count latch-driver 90. The rate count latch-driver 90 is connected by output buffers 92 with the infusion pump B. The output buffers 92 convert the digital count from the latch-driver 90 into binary coded decimal. The binary coded decimal rate control signal drives the infusion pump to cause medication to be introduced at the controlled rate. The rate count latch-driver 90 is connected with an LED display 94 for indicating to the attending nurse the count selected by the logic means 40. Another LED display 96 is connected with the output buffers for producing a display indicating the rate at which the infusion pump is introducing medication into the patient.

In the preferred embodiment, the infusion pump B can also be operated manually. As is conventional, the infusion pump has a manual rate selection switch 100 mounted within its housing. The manual rate selection switch 100 can be used to control the medication introduction rate independent the control means C. A manual/automatic selection switch 102 is used to select between the automatically determined medication introduction rate held in latch-driver 90 or the manually selected medication introduction rate determined by manual rate selection switch 100.

Figure 3A:
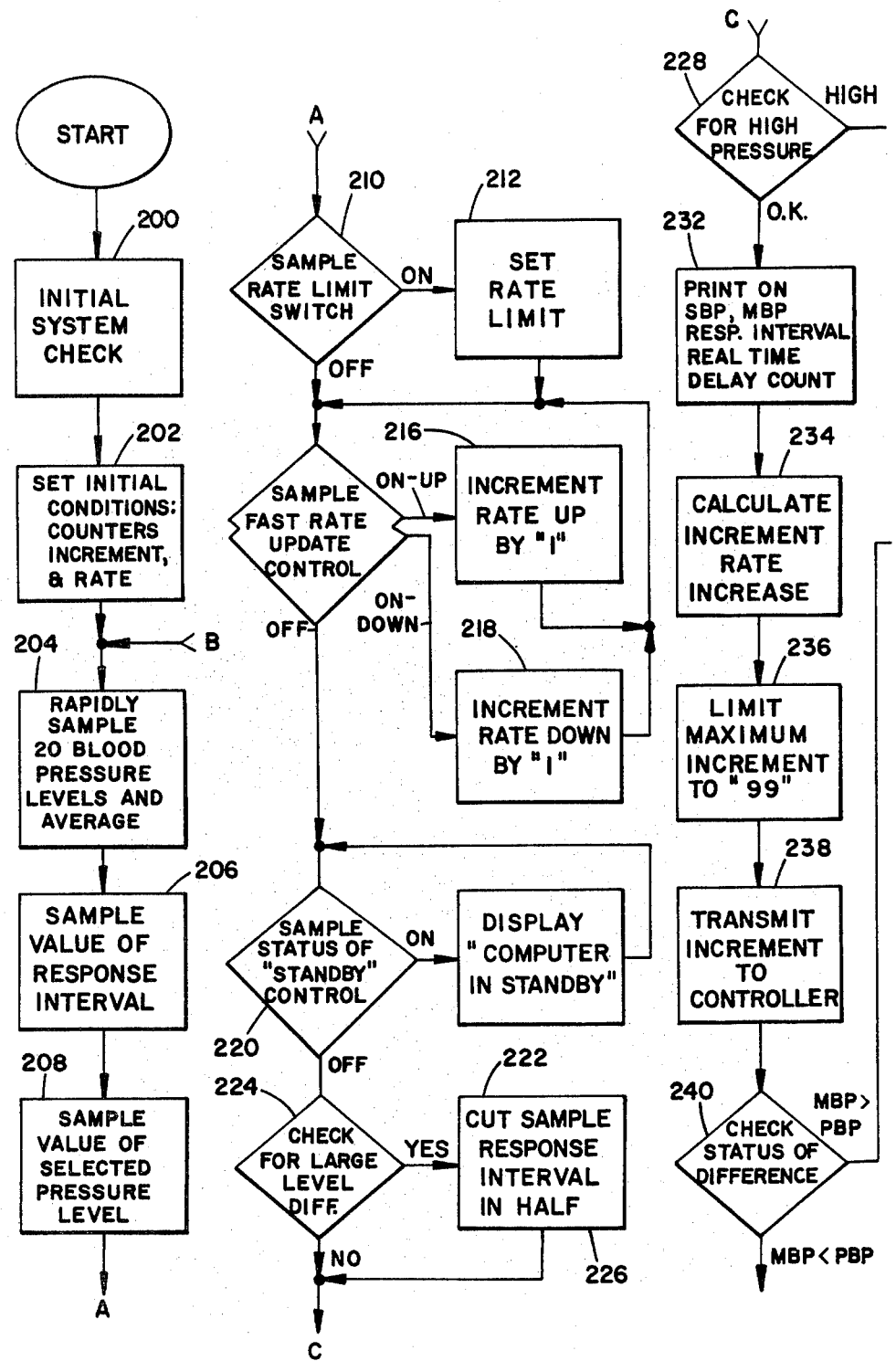
FIGS. 3A and 3B are a flow chart of preferred logic for implementing the present invention with a programmable computer.
Figure 3B:
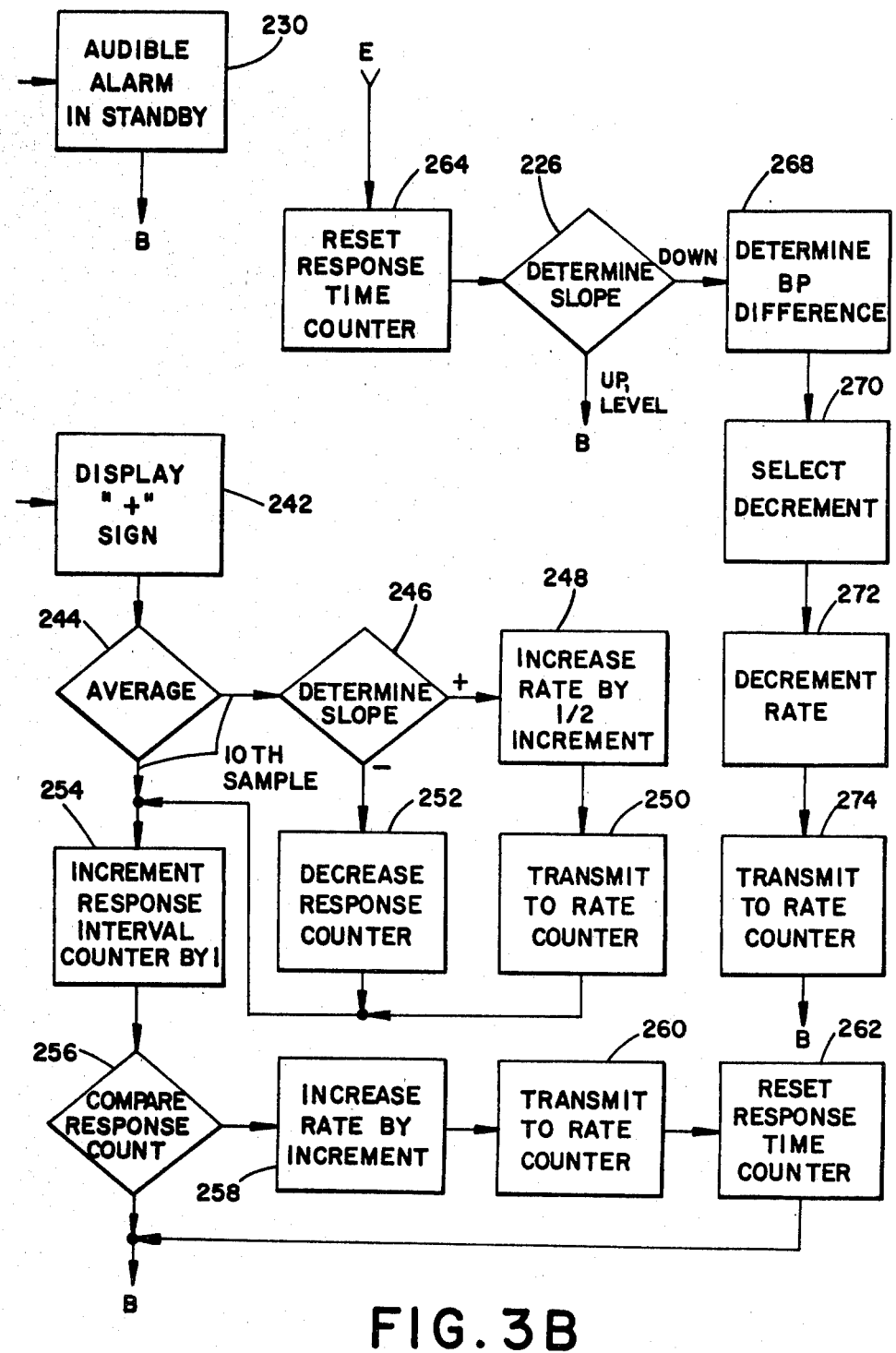

In the preferred embodiment, the logic means 40 is a programmable micro or mini-computer. FIGS. 3A and 3B are illustrative of a logic flow chart for programming the micro-computer to carry out the above described logic functions. Rather than describe a specific program which is, of course, limited to a single language, a programming logic flow chart is described below so that those of ordinary skill in the art may use the programming language or their choosing. A first step 200 is a self-test routine which checks the displays, the processor interfacing, the cable connections and the like to be sure that all is in proper working order. Once it is determined that all is in proper working order, a second step 202 sets the initial conditions on the various counters and in the various increment and rate storage memories.

Having initialized the computer, the programming goes into a cyclical monitoring loop. In step 204, twenty monitored blood pressure levels are sampled from the analog to digital converter 22 and averaged. This step is analogous to the function performed by averaging means 44 above. At step 206, the preselected response interval selected by selector switch 12 is sampled from the analog to digital converter 22. At step 208, the preselected blood pressure level set by switch 10 is sampled from the analog to digital converter.

The next step, step 210 is an optional safety check. In the preferred embodiment, there is a switch for limiting the maximum medication introduction rate to 99 drops per minute. If the rate limit switch is on, at step 212, the program limits the maximum medication introduction rate to 99 drops per minute. If the switch is off, the rate may go higher than 99 drops per minute. At step 214, the program checks the position of rate update switch 14. If switch 14 is in a manual medication introduction rate increase mode, the program goes into a loop at step 216 in which it repetitively increases the rate count by one until the rate count either reaches the maximum limit or switch 14 is moved from the increase position. If switch 14 is in a rate decrease position, the program goes into a loop at step 218 in which it repetitively decreases the rate count by one until the switch is moved from the decrease rate position. If the switch 14 is in the neutral or off position, the program moves to step 220 in which it monitors the position of standby control switch 16. If the standby control switch is in the "on" position, the program goes into a loop at step 222 in which it displays the legend "computer in standby" on the display means D.

If the standby control switch 16 is in the off position, the program moves to step 224 in which it checks whether there is a large differential between the monitored and selected levels. In the preferred embodiment, the large differential is 25 mmHg but other differences in the levels may be selected. If the difference is large, at step 226, the program cuts the response interval indicated by switch 12 in half to allow the patient's blood pressure to be brought more quickly toward the desired blood pressure level.

After checking for a large differential in the levels, the program performs another safety check at step 228. In this check, the program determines whether the monitored blood pressure level exceeds 225 mmHg. The 225 mmHg level is selected in the preferred embodiment because that is the level which would be indicated if there were a break in the line between the monitor and the analog to digital converter. Other levels may, of course, be chosen. If the patient's blood pressure level exceeds the high pressure level, at step 230, an audible alarm is sounded and the computer returns to step 204 to sample the monitor again. If the patient's blood pressure is below the high pressure level, at step 232 the program causes the display means D to display various information such as, the preselected blood pressure level, the monitored blood pressure level, the response interval, the real time delay count, and the like.

Analogous to the rate selection means 80, the program at step 234 calculates the incremental rate increase from the magnitude of the difference between the monitored and selected levels determined at step 224. If the 99 drops per minute limit switch is on, at step 236 the program limits the incremental rate increase to 99. At step 238, the program causes the rate increment to be stored.

The program at step 240 makes a second determination of the difference between the preselected and monitored levels. Step 240 finds analogy in the comparator means 46 of FIG. 2.

Analogous to rate of change means 60 of FIG. 2, if the monitored blood pressure is greater than the preselected blood pressure level, at step 242 the program causes a plus symbol (+) to be displayed on the display means D to indicate that the patient's blood pressure is rising. Analogous to averaging means 62, at step 244 the program averages ten monitored blood pressure levels. Analogous to comparing means 64 and temporary storage means 66, at step 246 the slope or rate of change in the monitored blood pressure is measured. If the patient's blood pressure is increasing, analogous to incremental rate selection means 80, step 248 increases the rate control counter by one half the increment calculated at step 234. At step 250, this increase increment is transmitted to the rate control counter. If the slope is negative, at step 252, the program increases the time remaining in the response interval. The response interval is measured with a counter which counts one unit about every two and one half seconds. To set the counter back twenty five seconds, at step 252 "10" is subracted from the counter.

Analogous with limiting means 52 and interval timer 56, at step 254 the response interval counter is incremented by one. In this manner, the response interval counter is increased by one each time the program passes through this point in the loop. In the preferred embodiment, this happens about every two and one half seconds. In this manner, the response interval counter functions as a timing means for timing the response interval. At step 256, the response counter is compared with the preselected response interval set by switch 12 and, if appropriate, adjusted at step 226. If the response interval has not yet elapsed, i.e., if the response counter has not yet counted to the response interval count, the program returns to step 204 and repeats another cycle through the program. If the response counter indicates that the selected response interval has elapsed, the medication introduction rate is increased at step 258 by the increment calculated in step 234 and stored in step 238. In step 260, the increase is transmitted to the rate control counter and in step 262 the response time counter is reset.

Returning to step 240, if the monitored blood pressure level is less than the preselected blood pressure level, the program moves to step 264 which like step 262 resets the response time count. Analogous with rate decrease means 70, at step 266 the program determines whether the monitored blood pressure is increasing toward the preselected level or decreasing further away from it. If the monitored blood pressure is increasing toward the preselected level, the program returns to step 204 and begins another monitoring cycle. Step 266 uses an up/down counter technique for determining whether the slope is positive or negative. With this technique, if the slope is decreasing, the magnitude of the output signal is related to the lesser of the difference between the presently monitored blood pressure level and the preselected blood pressure level or the difference between the presently monitored blood pressure level and a precedingly monitored blood pressure level. At step 268, the magnitude of the blood pressure difference for which compensation is to be made is determined. Analogous to decremental rate selection means 84, at step 270 the amount by which the rate control counter is to be decremented is selected. At step 272, the rate is decremented by the selected value and at step 274 the new rate is transmitted to the rate control counter. After step 274, the program returns to step 204 and commenses another cycle.

It will be appreciated that by using time sharing techniques or the like, a computer programmed in accordance with the above-described flow chart can be used to control a plurality of medication introducing means in response to a plurality of physiological condition monitors. In addition to having a separate monitor and medication introducing means for each patient, separate counters and storage areas would be designated in the computer for each patient.

The invention has been described with reference to the preferred embodiment. Various modifications and alterations will become apparent to others upon reading and understanding the preceding detailed description of the preferred embodiment. It is our intention that our invention include all such modifications and alterations which come within the scope of the appended claims or the equivalents thereof.

Having thus described a preferred embodiment of our invention, we now claim our invention to be:

1. A medication introduction rate control system comprising:
   a blood pressure monitor for monitoring a patient's blood pressure;
   an analog to digital converter operatively connected with the monitor for producing digital monitor signals which are indicative of the patient's blood pressure;
   a computer means for deriving from the monitor signals a rate control signal which indicates a rate of medication introduction, the computer means being operatively connected with the analog to digital converter the computer means including:
   comparing means for comparing the monitor signals with a preselected blood pressure level;
   rate of change means for periodically determining a rate of change of the monitor signals; and
   incremental rate selection means for adjusting the rate control signal in preselected increments which preselected increments are independent of a magnitude of a difference between the monitor signals and the preselected blood pressure level, the incremental rate selection means being operatively connected with the comparing means and the rate of change means, whereby the rate control signal is adjusted incrementally in response to the monitor signal and the preselected blood pressure level comparison and in response to the periodic rate of change determination;
   a latch means for temporarily storing the rate control signal, the latch means being operatively connected with the computer means.

2. The control system as set forth in claim 1 wherein the computer means is programmed to derive the rate control signal with the steps of:
   (a) comparing the monitor signals with the preselected blood pressure level;
   (b) if a monitor signal is above the preselected level, determining whether the monitor signals are increasing or decreasing;
   (c) if the monitor signals are increasing in step (b), increasing the rate control signal;
   (d) after determining whether the monitor signals are increasing or decreasing in step (b), incrementing a response interval count;
   (e) comparing the response interval count with a predetermined interval count;
   (f) if the response interval count is equal to or greater than the predetermined interval count, increasing the rate control signal;
   (g) if the response interval count is less than the predetermined interval count, and after step (f), returning to step (a);

(h) if in step (a) the monitor signal is less than the preselected blood pressure level, determining whether the monitor signals are increasing or decreasing;

(i) if the monitor signals are decreasing in step (h), decreasing the rate control signal;

(j) if the monitor signals are increasing in step (h) and after step (j), returning to step (a).

3. The control system as set forth in claim 1 further including an infusion pump for introducing blood pressure controllng medication into the patient, the infusion pump being operatively connected with said latch means.

4. A closed loop, medication introduction control system for controlling the rate at which a medication is introduced into a patient responsive to changes in a physiological condition of the patient, the system comprising:

a monitor for monitoring the level of the physiological condition, the monitor producing a monitor signal which varies with the changes in the monitored physiological condition level;

means for introducing medication into the patient at a controllable medication introduction rate;

rate controlling means for variably controlling the medication introduction rate, the rate controlling means including incremental rate selection means for increasing the medication introduction rate in preselected increments, the preselected increments being independent of a difference between the monitored physiological condition level and a preselected level of the physiological condition, whereby overmedication in response to a large difference between the monitored and preselected physiological condition levels is inhibited, the rate controlling means being operatively connected with the medication introducing means;

comparator means for comparing the monitor signal with the preselected level of said physiological condition, said comparator means having a first comparator output which is operatively connected with said incremental rate selection means for incrementally increasing the medication introduction rate in the preselected increments when the monitor signal exceeds the preselected level and a second comparator output which is operatively connected with said rate controlling means for decreasing the medication introduction rate when the preselected level exceeds the monitor signal;

limiting means operatively connected with the first comparator output and the rate controlling means for variably adjusting the time between successive medication introduction rate increases to a preselected minimum interval; and, rate of change means for determining the rate of change of the monitor signals, the rate of change means producing a first rate of change output when the monitor signals are increasing and a second rate of change output when the monitor signals are decreasing, the rate of change means being operatively connected with the rate controlling means for adjusting the medication introduction rate in response to the determined rate of change.

5. The system as set forth in claim 4 wherein said introducing means is an infusion pump.

6. The system as set forth in claim 5 wherein said monitor is a blood pressure monitor for monitoring the patient's blood pressure level whereby the physiological condition is the patient's blood pressure.

7. The system as set forth in claim 4 wherein the first rate of change means output is operatively connected with the incremental rate selection means for increasing the medication introduction rate in the preselected intervals and wherein the second rate of change output is operatively connected with said limiting means for lengthening said preselected minimum interval.

8. The system as set forth in claim 7 wherein said rate of change means includes temporary storage means for storing a preceding monitor signal and a comparing means for comparing the precedingly monitor signal with a currently monitor signal to determine whether the monitor signal is increasing or decreasing.

9. The system as set forth in claim 8 wherein the rate of change means further includes means for averaging a plurality of monitor signals, the temporary storage means being operatively connected with the averaging means for storing the averaged monitor signal for comparison with a subsequent averaged monitor signal and wherein said comparing means is operatively connected with the averaging means as well as the temporary storage means, whereby the rate of change is determined from an averaged plurality of monitor signals and a preceding averaged plurality of monitor signals.

10. The system as set forth in claim 7 further including difference means for determining the difference between the monitor signal and preselected level, the difference means being enabled by the second comparator output, a decrement rate selection means for selecting an amount of decrease in the medication introduction rate, the decrement rate selection means being operatively connected with said difference means and with said rate controlling means, whereby when the monitor signal is below the preselected level, the medication introduction rate is decreased by an amount corresponding to the difference between the monitor signal and preselected level.

11. The system as set forth in claim 10 further including a second rate of change means for enabling the difference means when the monitor signals are decreasing and for disabling the difference means when the monitor signals are increasing, the second rate of change means being operatively connected with the second comparator output.

12. The system as set forth in claim 7 further including rate decreasing means for causing the rate controlling means to decrease the controlled medication introduction rate when the preselected level exceeds the monitor signal, the rate decresing means being operatively connected with the second comparator output.

13. The system as set forth in claim 12 wherein the rate controlling means further includes an up-down counter means, the output of the counter means indicating the controlled medication introduction rate.

14. The system as set forth in claim 7 further including a monitor signal averaging means for averaging a plurality of monitor signals, the monitor signal averaging means being operatively connected with the monitor and the comparator means.

15. The system as set forth in claim 14 further including an analog to digital conversion means operatively connected with the monitor for converting the monitor signals from analog to digital.

16. A medication introduction control system comprising:

an analog to digital converter which is adapted to convert sampled analog signals from a physiological condition monitor to digital monitor signals;

averaging means for averaging a plurality of the digital monitor signals, the averaging means being operatively connected with analog to digital converter;

comparator means for comparing the averaged digital monitor signals with a preselected level, said comparator means having a first comparator output which indicates that an averaged digital monitor signal is above the preselected level and a second comparator output which indicates that the averaged digital monitor signal is below the preselected level, the comparator means being operatively connected with the averaging means;

rate increasing means for increasing the rate of medication introduction, the rate increasing means being operatively connected said first comparator output for increasing the rate by a first amount in response thereto;

rate controlling means for producing a rate signal which is adapted to control the rate of an infusion pump, the rate controlling means being operatively connected with the rate increasing means, whereby the rate signal is increased when the averaged digital monitor signal is above the preselected level;

limiting means operatively connected with the first comparator output and the rate increasing means for variably adjusting the time duration between successive increases to a preselected minimum time interval;

rate of change means for determining the rate of change of the averaged digital monitor signals, the rate of change means having a first rate of change output which indicates that the averaged digital monitor signals are increasing and a second rate of change output which indicates that the averaged digital monitor signals are decreasing, the rate of change means being operatively connected with the averaging means, the first rate of change output being operatively connected with the rate increasing means for increasing the rate by a second amount, the second rate of change output being operatively connected with the limiting means for increasing said preselected minimum time interval; and, rate decreasing means for decreasing the rate of medication introduction, the rate decreasing means being operatively connected with the comparator second output and with the rate controlling means whereby the rate signal is decreased when the averaged digital monitor signal is below the preselected level.

17. A method of controlling a rate at which a medication is introduced into a patient responsive to changes in a physiological condition of the patient, the method comprising:

(A) introducing the medication into the patient substantially continuously at a controllable medication rate;

(B) monitoring the physiological condition as the medication is introduced into the patient and producing a monitor signal which indicate a monitored level of the physiological condition;

(C) comparing the monitor signal with a preselected level of the physiological condition to determine whether the monitored level exceeds the preselected level;

(1) if the monitored level fails to exceed the preselected level:

(a) determining whether the monitored level is decreasing:

(i) if the monitored condition is decreasing, decreasing the medication rate and returning to step B;

(ii) if the monitored condition is not decreasing, returning to step B;

(2) if the monitored levels exceeds the preselected level:

(a) increasing the medication rate by a preselected first incremental amount, which first incremental amount is independent of the magnitude of a difference between the monitored level and the predetermined level, whereby increases in the medication rate are independent from the magnitude by which the monitored level exceeds the predetermined level; and, (b) determining whether the monitored level is increasing:

(i) if the monitored levels is increasing, further increasing the medication rate by a second incremental amount and returning to step B;

(ii) if the monitored levels is not increasing, returning to step B.

18. The method as set forth in claim 17 wherein the monitoring step (B) includes averaging a predetermined plurality of monitor signals such that in step (C) an averaged monitor signal is compared with the preselected level.

19. The method as set forth in claim 18 further including after step (C)(2)(b)(ii), the step of decreasing a time interval between step (C) comparisons.

* * * * *